(12) United States Patent
Sun et al.

(10) Patent No.: US 9,156,746 B2
(45) Date of Patent: Oct. 13, 2015

(54) USE OF BYPRODUCT ACETIC ACID FROM OXIDATIVE METHODS OF MAKING ACRYLIC ACID AND/OR METHACRYLIC ACID

(71) Applicants: Archer Daniels Midland Company, Decatur, IL (US); Washington State University, Pullman, WA (US)

(72) Inventors: Junming Sun, Pullman, WA (US); Changjun Liu, Pullman, WA (US); Yong Wang, Pullman, WA (US); Kevin Martin, Mt. Zion, IL (US); Padmesh Venkitasubramanian, Forsyth, IL (US)

(73) Assignees: Washington State University, Washington; Archer Daniels Midland Co., Decatur ( * ) Notice: Subject to any disclaimer, the term of this patent is extended or adjusted under 35 U.S.C. 154(b) by 0 days.

(21) Appl. No.: 14/683,263

(22) Filed: Apr. 10, 2015

(65) Prior Publication Data

US 2015/0210607 A1    Jul. 30, 2015

Related U.S. Application Data

(63) Continuation of application No. PCT/US2013/062784, filed on Oct. 1, 2013, and a continuation of application No. PCT/US2013/063968, filed on Oct. 9, 2013, and a continuation of application No. PCT/US2013/067053, filed on Oct. 28, 2013.

(60) Provisional application No. 61/720,433, filed on Oct. 31, 2012, provisional application No. 61/737,312, filed on Dec. 14, 2012, provisional application No. 61/856,895, filed on Jul. 22, 2013.

(51) Int. Cl.
| | | |
|---|---|---|
| C07C 1/207 | (2006.01) |
| C07C 51/16 | (2006.01) |
| C07C 41/06 | (2006.01) |
| C07C 2/86 | (2006.01) |
| C07C 2/06 | (2006.01) |
| C07C 5/03 | (2006.01) |

(52) U.S. Cl.
CPC ............... *C07C 1/2078* (2013.01); *C07C 2/06* (2013.01); *C07C 2/867* (2013.01); *C07C 5/03* (2013.01); *C07C 41/06* (2013.01); *C07C 51/16* (2013.01); *C07C 2523/06* (2013.01)

(58) Field of Classification Search
None
See application file for complete search history.

(56) References Cited

U.S. PATENT DOCUMENTS

2014/0121430 A1* 5/2014 Sun ................... C07C 1/2078
                                                            585/321
2014/0128650 A1* 5/2014 Sun ..................... C07C 5/48
                                                            585/327
2015/0218077 A1* 8/2015 Sun ................... C07C 51/252
                                                            562/532

FOREIGN PATENT DOCUMENTS

| WO | 2014204509 | * 12/2014 |
| WO | 2014204510 | * 12/2014 |
| WO | 2015005941 | *  1/2015 |

OTHER PUBLICATIONS

Crisci et al., ACS Catalysis (2014), 4(11), 4196-4200.*

* cited by examiner

*Primary Examiner* — Karl J Puttlitz
(74) *Attorney, Agent, or Firm* — William B. Miller

(57) ABSTRACT

Processes are described for improved utilization of the byproduct acetic acid universally produced in various oxidative processes for making acrylic acid and methacrylic acid, wherein at least a portion of the byproduct acetic acid is converted to isobutene and optionally to one or more further value-added products which may be prepared from isobutene.

7 Claims, No Drawings

USE OF BYPRODUCT ACETIC ACID FROM OXIDATIVE METHODS OF MAKING ACRYLIC ACID AND/OR METHACRYLIC ACID

CROSS-REFERENCE TO RELATED APPLICATIONS

The present application is a continuation of International Application No. PCT/US2013/067053, filed Oct. 28, 2013, now published as WO 2015/012876, which directly claims the benefit of U.S. Provisional Application Ser. No. 61/856,895, filed Jul. 22, 2013; the present application is also a continuation of International Application No. PCT/US2013/063968 filed Oct. 9, 2013, now published as WO 2014/092849, which directly claims the benefit of U.S. Provisional Application Ser. No. 61/737,312 filed Dec. 14, 2012; and, the present application is also a continuation of International Application No. PCT/US2013/062784 filed Oct. 1, 2013, now published as WO 2014/070354, which directly claims the benefit of U.S. Provisional Application Ser. No. 61/720,433 filed Oct. 31, 2012.

TECHNICAL FIELD

The present invention relates to methods for producing acrylic acid and methacrylic acid, and more particularly to the development of productive uses for the byproducts of such methods.

BACKGROUND ART

It is well known in the commercial production of crude acrylic acid by the oxidation of acrolein as well as in the commercial production of methacrylic acid by the oxidation of methacrolein that various byproducts are invariably also formed, including acetic acid. More particularly and by way of example, in the production of acrylic acid these various byproducts can include, in addition to acetic acid, propionic acid, water, acrylic acid dimers, acrolein, benzaldehyde, furfurals and hydroquinone. Conventionally, manufacturers have been led to adopt a number of purification methods to remove these byproducts to an extent whereby the purified acrylic acid (glacial acrylic acid) can be used in subsequent conversions, especially in polymerization processes wherein the purified acrylic acid or an acrylate prepared therefrom is used as a monomer.

Acetic acid and propionic acid are recognized as particularly problematic in that both are saturated and cannot be polymerized, so that depending on the polymerization process involved and the applications targeted for the polymer, these impurities may remain in the finished product and risk conferring undesirable corrosive properties on the finished product or being reencountered as waste in the liquid or gaseous discharges from the polymerization process. While propionic acid is removed from the crude acrylic acid product only with great difficulty and at significant expense, inasmuch as the difference in boiling points between propionic and acetic acids is very small, acetic acid can be removed to an extent in a light fraction by conventional distillation methods.

Unfortunately, while the amount of byproduct acetic acid produced varies in known processes for making acrylic acid or methacrylic acid through acrolein and methacrolein intermediates, respectively, dependent in part on what starting material or materials are employed, whether propylene or glycerol for acrylic acid manufacture or isobutene, isobutyraldehyde, t-butanol, isobutanol and the like for methacrylic acid manufacture—for example, up to about 5 percent by weight for acrolein produced from propylene and up to about 10 percent by weight for acrolein produced from glycerol—nevertheless the amounts produced are all substantial as compared to a desired content of less than about 0.1 percent by weight of acetic acid in a glacial acrylic acid finished product. Consequently, whatever the feed and process for making acrylic acid via acrolein oxidation and/or for making methacrylic acid via methacrolein oxidation and whatever the particular method used or proposed to be used for separating out the substantial byproduct acetic acid, a substantial yield loss of acrylic acid has accompanied or has been understood as necessarily coincident with removing the acetic acid down to the requirements of glacial acrylic acid, and this is particularly so with the production of a biobased acrylic acid as intensively researched in recent years.

Acrylic acid has also been prepared by oxidative methods other than through an acrolein intermediate. More particularly, methods have been described for making acrylic acid from propane according to a redox mechanism. U.S. Pat. No. 6,833,474 to Dubois, U.S. Pat. No. 7,332,625 to Dubois et al. and U.S. Pat. No. 7,345,198 to Dubois et al. provide examples of such methods from one company, wherein a gaseous mixture comprising propane, steam or water vapor and optionally an inert gas is passed over catalysts of a prescribed character in the further presence of molecular oxygen (U.S. Pat. No. 7,332,625 and U.S. Pat. No. 7,345,198) or in the absence of molecular oxygen (U.S. Pat. No. 6,833,474), and the propane is oxidized to acrylic acid. In these oxidative methods, as well, acetic acid is produced as a byproduct.

SUMMARY OF THE INVENTION

The present invention relates to use of byproduct acetic acid from an oxidative process for making acrylic acid or from an oxidative process for making methacrylic acid to make isobutene. In certain embodiments, the isobutene so formed is itself converted at least in part to one or more additional value-added products. In one embodiment, isobutene is used to make methacrylic acid. In another embodiment, isobutene prepared from byproduct acetic acid is used to make isoprene, while in other embodiments, isobutene from byproduct acetic acid is used to make methyl tertiary butyl ether or ethyl tertiary butyl ether. In still other embodiments, isobutene from the byproduct acetic acid is used to make butylated hydroxytoluene or butylated hydroxyanisole. In still another embodiment, isobutene is used to make isooctane.

DESCRIPTION OF EMBODIMENTS

Isobutene is widely used for the production of a variety of industrially important products, including but not being limited to those named in the preceding paragraph. Isobutene has however been produced commercially to date through the catalytic or steam cracking of fossil feedstocks. As fossil resources are depleted and/or become more costly to use, renewable source-based routes to isobutene are increasingly needed—especially in consideration of increased demand for isobutene. Concurrently, the same considerations have spurred a significant amount of research into renewable source-based routes to acrylic acid and other large-scale chemical products; at least one of the primary routes, from glycerol, has been found as indicated in U.S. Pat. No. 8,440,859 to Dubois to produce substantial amounts of acetic acid as an unwanted byproduct.

Our discovery, per our U.S. Patent Application Ser. No. 61/737,312 (the "'312 application") filed Dec. 14, 2012 for "Process and Catalyst for Conversion of Acetic Acid to Isobutene", that one may convert acetic acid to a wholly biobased isobutene in the presence of a $Zn_xZr_yO_z$ mixed oxide catalyst can thus be seen to address both the need for a viable renewable source-based method for making a biobased isobutene product as well as the need for an improved and more economical process for making a biobased acrylic acid product, particularly in consideration of the substantial amounts of byproduct acetic acid generated in the glycerol-based methods. This having been said, those skilled in the art will appreciate even in consideration of the conventional fossil fuel-based oxidative methods for making acrylic acid and/or methacrylic acid, the diverse value-added product opportunities enabled by the capability to convert byproduct acetic acid to isobutene can materially improve the overall economics of even these fossil fuel-based methods, while also providing the desired biobased isobutene product.

Previous to our U.S. Patent Application Ser. No. 61/720,433 filed Oct. 31, 2012 for "Stable Mixed Oxide Catalysts for Direct Conversion of Ethanol to Isobutene and Process for Making" (the "'433 application"), a hard-template method had been described for synthesizing $Zn_xZr_yO_z$ mixed oxides for the direct and high yield conversion of ethanol (from the fermentation of carbohydrates from renewable source materials, including biomass) to isobutene, wherein ZnO was added to $ZrO_2$ to selectively passivate zirconia's strong Lewis acidic sites and weaken Brönsted acidic sites while simultaneously introducing basicity. The objectives of the hard template method were to suppress ethanol dehydration and acetone polymerization, while enabling a surface basic site-catalyzed ethanol dehydrogenation to acetaldehyde, an acetaldehyde to acetone conversion via aldol-condensation/dehydrogenation, and a Brönsted and Lewis acidic/basic site-catalyzed acetone-to-isobutene reaction pathway.

High isobutene yields were in fact realized, but unfortunately, as later experienced by Mizuno et al. (Mizuno et al., "One-path and Selective Conversion of Ethanol to Propene on Scandium-modified Indium Oxide Catalysts", *Chem. Lett.*, vol. 41, pp. 892-894 (2012)) in their efforts to produce propylene from ethanol, it was found that further improvements in the catalyst's stability were needed.

The '433 application concerns the discovery that these improvements could be realized without adding modifying metals and without a reduction in the initial high activity (100 percent ethanol conversion) that had been observed in these mixed oxide catalysts. The '433 application thus in sum concerns an improved stability, longer lifetime catalyst for converting ethanol to isobutene.

Separately, we discovered that the catalyst of the '433 application may also be used for converting acetic acid, rather than ethanol, to a biobased isobutene product. This discovery became the basis for the above-referenced '312 application, which was filed shortly after the '433 application.

Parenthetically, by "biobased", we mean those materials whose carbon content is shown by ASTM D6866 to be derived from or based in significant part (at least 20 percent or more) upon biological products or renewable agricultural materials (including but not being limited to plant, animal and marine materials) or forestry materials. "Wholly biobased" thus will be understood as referring to materials whose carbon content by ASTM D6866 is entirely or substantially entirely (for example, 95 percent or more) indicated as of biological origin.

In this respect ASTM Method D6866, similar to radiocarbon dating, compares how much of a decaying carbon isotope remains in a sample to how much would be in the same sample if it were made of entirely recently grown materials. The percentage is called the biobased content of the product. Samples are combusted in a quartz sample tube and the gaseous combustion products are transferred to a borosilicate break seal tube. In one method, liquid scintillation is used to count the relative amounts of carbon isotopes in the carbon dioxide in the gaseous combustion products. In a second method, 13C/12C and 14C/12C isotope ratios are counted (14C) and measured (13C/12C) using accelerator mass spectrometry. Zero percent 14C indicates the entire lack of 14C atoms in a material, thus indicating a fossil (for example, petroleum based) carbon source. One hundred percent 14C, after correction for the post-1950 bomb injection of 14C into the atmosphere, indicates a modern carbon source. ASTM D6866 effectively distinguishes between biobased materials and petroleum derived materials in part because isotopic fractionation due to physiological processes, such as, for example, carbon dioxide transport within plants during photosynthesis, leads to specific isotopic ratios in natural or biobased compounds. By contrast, the 13C/12C carbon isotopic ratio of petroleum and petroleum derived products is different from the isotopic ratios in natural or bioderived compounds due to different chemical processes and isotopic fractionation during the generation of petroleum. In addition, radioactive decay of the unstable 14C carbon radioisotope leads to different isotope ratios in biobased products compared to petroleum products.

The $Zn_xZr_yO_z$ mixed oxide catalysts in question are generally characterized by a Zn/Zr ratio (x:y) of from 1:100 to 10:1, preferably from 1:30 to 1:1, especially about 1:20 to about 1:5, and still more preferably about 1:12 to about 1:10.

Parenthetically, in the present application where any range of values is given for any aspect or feature of the mixed oxide catalysts or any process described for using the mixed oxide catalysts, the given ranges will be understood as disclosing and describing all subranges of values included within the broader range. Thus, for example, the range of 1:100 to 10:1 will be understood as disclosing and describing not only the specific preferred and more preferred subranges given above, but also every other subrange including a value for x between 1 and 10 and every other subrange including a value for y between 1 and 100.

The catalysts made by the method of the '433 application and preferred for use in the acetic acid to isobutene conversion are consistent in their particle size with catalysts made by the hard template method described in Sun et al., "Direct Conversion of Bio-ethanol to Isobutene on Nanosized $Zn_xZr_yO_z$ Mixed Oxides with Balanced Acid-Base Sites", Journal of the American Chemical Society, vol. 133, pp 11096-11099 (2011), wherein carbon black (BP 2000 carbon black from Cabot Corp.) was used as a hard template for the synthesis of nanosized $Zn_xZr_yO_z$ mixed oxides. In the hard template method of manufacture described in Sun, the BP 2000 template was dried at 180° C. overnight. Calculated amounts of zirconyl nitrate hydrate (Sigma-Aldrich, greater than 99.8% purity) and $Zn(NO_3)_2.6H_2O$ (Sigma-Aldrich, greater than 99.8% purity) were dissolved in a given amount of water, and sonicated for 15 minutes to produce a clear solution with desired concentrations of Zn and Zr. About 25 grams of the obtained solution were then mixed with 6.0 grams of the preheated BP 2000 to achieve incipient wetness, and the mixture was transferred to a ceramic crucible and calcined at 400 degrees Celsius for 4 hours, followed by ramping the temperature to 550 degrees Celsius (at a ramp rate of 3 degrees Celsius/minute) and holding at 550 degrees Celsius for another 20 hours. Nanosized white powders were obtained, having a mean particle size of less than 10 nanometers. The catalysts made by the method of the '433 application and preferred for use in the acetic acid to isobutene conversion likewise comprise aggregates of less than 10 nm-sized particles, with a highly crystalline structure. The Zn oxide component is again highly dispersed on the Zr oxide component.

As summarized in the '433 application, some characteristic differences have, however, also been observed between catalysts of equivalent Zn/Zr ratios made by the prior hard template method and by the method of the '433 application. For example, average crystallite size as calculated based on the Scherer equation will typically be larger, for example, approximately 8.4 nanometers for a $Zn_1Zr_{10}O_2$ mixed oxide catalyst prepared according to the '433 application as compared to 4.8 nanometers for a $Zn_1Zr_{10}O_2$ mixed oxide catalyst prepared according to the former hard template method.

A $Zn_1Zr_{10}O_2$ mixed oxide catalyst prepared according to the method of the '433 application also has a smaller surface area, approximately 49 square meters per gram, as compared to 138 square meters per gram for a $Zn_1Zr_{10}O_2$ mixed oxide catalyst prepared according to the former hard template method.

One further, compositional difference was also observed between catalysts prepared by the two methods, in that the $Zn_xZr_yO_z$ mixed oxide catalysts according to the '433 application preferably are substantially sulfur-free, containing less than 0.14 weight percent of sulfur, as compared to, for example, 3.68 weight percent of sulfur in the same $Zn_1Zr_{10}O_2$ mixed oxide catalyst prepared according to the former hard template method. Preferably, the catalysts used herein have a sulfur content of less than 0.01 percent by weight, and still more preferably the catalysts will have a sulfur content of less than 0.001 percent by weight.

Based on infrared analyses of catalysts prepared according to the '433 application and according to the hard template method (which analyses are described more fully in the incorporated '433 application), while there were certain other differences that were noted (as just described), the presence of sulfur in the former catalysts—presumably left behind from the Cabot BP 2000 furnace black hard template after the template's being substantially removed by a controlled combustion—is believed to have contributed to the presence of a number of stronger Lewis and Brönsted acidic sites on catalysts made by the former method and in turn to have particularly contributed to a greater degree of acidic site-catalyzed coking of catalysts made according to the former hard template method, in the context of converting ethanol to isobutene.

The substantially sulfur-free catalysts of the '312 application preferred for use herein may be made by a process broadly comprising, in certain embodiments, forming a solution of one or more Zn compounds, combining one or more zirconium-containing solids with the solution of one or more Zn compounds so that the solution wets the zirconium-containing solids to a state of incipient wetness, drying the wetted solids, then calcining the dried solids. In other embodiments, a solution is formed of one or more Zr compounds, the solution is combined with one or more Zn-containing solids so that the solution wets the Zn-containing solids to a state of incipient wetness, the wetted solids are dried and then the dried solids are calcined. In principle, provided the zinc and zirconium compounds and solids in these embodiments do not contain sulfur, any combination of zinc and zirconium materials and any solvent can be used that will permit the zinc and zirconium components to mix homogeneously whereby, through incipient wetness impregnation, one of the zinc or zirconium components are well dispersed on a solid of the other component for subsequent drying and conversion to the oxide forms through calcining.

The conditions and times for the drying and calcining steps will depend, of course, on the particular zinc and zirconium materials and solvent used, but in general terms, the drying step can be accomplished in a temperature range of from 60 degrees Celsius to 200 degrees Celsius over at least 3 hours, while the calcining can take place at a temperature of from 300 degrees Celsius to 1500 degrees Celsius, but more preferably a temperature of from 400 to 600 degrees Celsius is used. The calcination time can be from 10 minutes to 48 hours, with from 2 to 10 hours being preferred.

In still other embodiments, suitable $Zn_xZr_yO_z$ mixed oxide catalysts can also be prepared by a hard template method, except that a suitable very low sulfur content carbon is used for the hard template such that the finished catalyst will contain not more than 2 percent by weight of sulfur, especially not more than 0.5 percent by weight of sulfur and still more preferably will contain not more than 0.1 weight percent (by total weight of the catalyst) of sulfur. A variety of such very low sulfur carbons are available commercially from various suppliers; in general, the lower the sulfur content, the better for forming the highly active, stable mixed oxide catalysts preferred for use in a process of the present invention.

In terms of the process for converting byproduct acetic acid (from an associated oxidative process for producing acrylic acid and/or methacrylic acid) to isobutene using such a catalyst, the process can be conducted continuously in the gas phase, using a fixed bed reactor or flow bed reactor. The reaction temperature may be in a range from 350 to 700 degrees Celsius, preferably, in a range from 400 to 500 degrees Celsius, and the WHSV can be in a range from 0.01 $hr^{-1}$ to 10 $hr^{-1}$, preferably from 0.05 $hr^{-1}$ to 2 $hr^{-1}$. Acetic acid/water solutions with steam to carbon ratios from 0 to 20, preferably from 2 to 5 can be used to provide acetic acid to the catalyst. An inert carrier gas, such as nitrogen, can be used as in Example 1 of the '312 application.

Once the isobutene is formed from the byproduct acetic acid consistent with the process of the '312 application, a number of value-added options are available to those of routine skill in the art, using known methods for converting the isobutene to other useful materials if desired. As already noted isobutene itself is commercially valuable, and if the byproduct acetic acid is wholly biobased—being derived for example from the dehydration of glycerol (from fat-splitting of triglycerides and as a byproduct of biodiesel processes) to acrolein and the subsequent oxidation of acrolein to acrylic acid—then a biobased isobutene may be obtained.

In one possible embodiment, the isobutene (or a portion thereof) can be oxidized with oxygen from an oxygen source to yield methacrolein according to any known process and using any known catalyst for this purpose, and the methacrolein may be further oxidized to produce a methacrylic acid product, again according to any known process and using any known catalyst for the second oxidation step from methacrolein to methacrylic acid. In this regard, a number of patents have been issued describing methods for producing methacrylic acid from isobutene via a methacrolein intermediate, though those skilled in the art will be aware that the following are given as merely non-limiting examples of the various processes and catalysts that have been and continue to be described in the patent and general scientific literature relating to a part of such a process or the process as a whole.

U.S. Pat. No. 8,273,313 to Galloway describes a system and process for separating methacrolein from methacrylic acid and acetic acid in the gas phase product from a partial oxidation of isobutene in two oxidation steps, purportedly maximizing recovery of all three components at minimum capital and energy cost, under conditions minimizing polymerization and plugging by solids deposition in compressors, columns and the like. A number of patents and publications are recited for disclosing aspects of a process of partially oxidizing isobutene or an isobutene equivalent into methacrylic acid in a single step or multi-step oxidation process, for example, U.S. Pat. No. 4,544,054; U.S. Pat. No. 4,618,709; U.S. Pat. No. 4,925,981; U.S. Pat. No. 4,956,493; U.S. Pat. No. 4,987,252; U.S. Pat. No. 5,356,460; U.S. Pat. No. 5,780,679 and WO 0345083.

U.S. Pat. No. 7,732,367 to Stevenson et al. concerns a catalyst for accomplishing the gas-phase methacrolein oxidation to methacrylic acid and methods of making the catalyst, where the catalyst includes at least molybdenum, phosphorus, vanadium, bismuth and a first component selected from potassium, rubidium, cesium, thallium or mixtures or combinations of these, has at least 57% medium pores and a nitric acid to molybdenum ratio of at least 0.5 to 1 or a nitric acid to $Mo_{12}$ ratio of at least 6.0:1.

U.S. Pat. No. 5,231,226 to Hammon et al. also relates particularly to the gas-phase oxidation of methacrolein to methacrylic acid, disclosing a process for the catalytic gas-phase oxidation of methacrolein to methacrylic acid in a fixed-bed reactor at elevated temperature on catalytically-active oxides with a single pass conversion of from 45 to 95 percent. Because of the exothermicity of the reaction, the reaction temperature is maintained from 280 to 340 degrees Celsius until a methacrolein conversion of from 20 to 40 percent is reached, at which point the reaction temperature is reduced at once, incrementally or continuously by from 5 to 40 degrees Celsius until a conversion of from 45 to 95 percent has been accomplished, with the proviso that the reaction temperature is not less than 260 degrees Celsius. Suitable catalysts are indicated as those described in EP 265733, EP 102688 and DE 3010434.

U.S. Pat. No. 5,155,262 to Etzkorn et al. concerns both processes for the oxidation of isobutene to methacrolein and for the oxidation of isobutene to methacrylic acid in two stages with methacrolein as an intermediate, wherein prior methods using steam in the starting reactant gas mixture to avoid flammable gas mixtures and to improve reaction selectivity are assertedly improved by using essentially inert, essentially anhydrous diluent gases in place of the steam. Reduced wastewater load, improved selectivity and reduced byproduct formation are said to result from the substitution. Etzkorn et al. recite that "many oxidation catalysts have been disclosed for producing methacrolein in high yield by oxidizing isobutene", col. 1, lines 60-62, giving as examples catalysts containing mixed oxides of molybdenum, bismuth and iron with phosphorus or tungsten or antimony, and commonly incorporating cobalt and/or nickel and alkali metals as promoters, col. 1, lines 62-65. For the second stage oxidation of methacrolein to methacrylic acid, mixed metal oxide catalysts are described which are said to typically contain molybdenum, vanadium, tungsten, chromium, copper, niobium, tantalum and antimony. Etzkorn et al. refer in this regard to a number of additional publications predating those listed in U.S. Pat. No. 8,273,313, including U.S. Pat. No. 4,147,885; U.S. Pat. No. 3,475,488; U.S. Pat. No. 3,171,859; U.S. Pat. No. 4,267,386 and U.S. Pat. No. 4,267,385, as well as UK 2,068,947 and U.S. Pat. No. 4,618,709.

In another embodiment, the isobutene (or at least a portion thereof) can be converted to isoprene according to any known process for doing so, for example, according to U.S. Pat. No. 4,511,751 to Ninagawa et al, U.S. Pat. No. 7,442,844 to Ninagawa et al., WO 09082260 to Busygin et al or EP 2157072 to Busygin et al. In U.S. Pat. No. 4,511,751, isobutene and a formaldehyde source are fed, together with water, into an acidic aqueous solution continuously or intermittently while maintaining the reaction pressure and distilling off the product isoprene and unreacted starting materials, together with water, from the reaction zone.

In another embodiment, the isobutene (or at least a portion thereof) can be converted to an alkyl tert-butyl ether, for example, methyl tert-butyl ether (MTBE) or ethyl tert-butyl ether (ETBE), according to any known process for doing so. The art contains a number of examples for making non-biobased, conventional MTBE, see, for example, U.S. Pat. No. 4,118,425 to Herbstman, U.S. Pat. No. 4,329,516 to Al-Muddarris, U.S. Pat. No. 4,423,251 to Pujado et al., U.S. Pat. No. 4,981,491 to Harandi et al., and U.S. Pat. No. 5,254,764 to Miracca et al., as well as Ullmann's Encyclopedia of Industrial Chemistry, 11th ed., "Methyl Tert-Butyl Ether", pp 119-130, Wiley-VCH Verlag GmbH & Co. KGaA, Weinheim (2012). The art also contains an example of a more recent integrated process for making isobutene, in part by the dissociation of MTBE formed initially to facilitate the separation of isobutene from the mixed C4 stream, see US 2012/0142985 to Winterberg et al. ETBE for its part has been made in a like manner as MTBE, through using ethanol rather than methanol in the etherification step of such processes.

In another embodiment, isobutene, isoprene and MTBE are all produced from the acetic acid, or isoprene and MTBE are produced as value-added products from the isobutene. In this last regard, U.S. Pat. No. 4,593,145 to Ninagawa et al. describes a process for producing isoprene, characterized in that an alkyl-t-butyl ether (e.g., methyl-t-butyl ether (MTBE) or ethyl-t-butyl ether (ETBE) as are still commercially manufactured and extensively used as antiknock fuel additives) and a formaldehyde source are fed, together with water, into an acidic aqueous solution continuously or intermittently while maintaining the reaction pressure in an adequate range and at the same time distilling off the product isoprene, unreacted starting materials, isobutene and tertiary butanol, together with water, from the reaction zone. Still other references supply isobutene and methanol directly rather than generating the same by cracking MTBE, oxidizing the methanol to formaldehyde with an oxygen source in the presence of an oxidation catalyst and then reacting the formaldehyde thus formed with the isobutene feed.

In another embodiment, the isobutene (or at least a portion thereof) can be converted to isooctane. A suitable process for making both alkyl-tert-butyl ethers and isooctane is described in Marchionna et al., "Light olefins dimerization to high quality gasoline components", Catalysis Today, Volume 65, Issues 2-4, 20 Feb. 2001, pages 397-403. In Marchionna et al's process, isobutene is partially etherified with an alcohol such as methanol, ethanol or isopropanol and concurrently is partially oligomerized into a di-isobutenes rich fraction, in a water cooled tubular reactor and in the presence of a catalyst. In a second stage, the di-isobutenes rich fraction is hydrogenated to an isooctane-based high quality alkylate. The partial etherification/dimerization catalyst is an ionic resin, particularly an acidic resin of a type sold under the Amberlyst® trademark. U.S. Pat. No. 6,767,372 to Barnes et al. describes a similar process, wherein MTBE from isobutene is converted to di-isobutylene (apparently completely) and the di-isobutylene is subsequently hydrogenated to isooctane, with using distillation to remove any trimers and other impurities formed.

In another embodiment, the isobutene (or at least a portion thereof) can be converted to either or both of the widely used antioxidants and food preservatives butylated hydroxytoluene and butylated hydroxyanisole. Butylated hydroxytoluene (BHT) has been known to be prepared by the reaction of isobutene with p-cresol (4-methylphenol) in the presence of sulfuric acid as a catalyst, see Fiege et al, "Phenol Derivatives", Ullmann's Encyclopedia of Industrial Chemistry, Wiley-VCH, Weinheim, 2002, while butylated hydroxyanisole (BHA) has been known to be prepared analogously by the reaction of 4-methoxyphenol and isobutene.

While the foregoing are examples of a number of value-added materials that could be made from the isobutene obtained from the byproduct acetic acid according to the '312 application, those skilled in the art will certainly appreciate that still other valuable materials could be made from the isobutene, and that the capacity to make isobutene and such other value-added products can have a material impact on the economic value of all of the known and future oxidative processes for making acrylic acid or for making methacrylic acid in which acetic acid is produced as a substantial byproduct, whether such processes are renewable source-based or conventionally dependent on propane or propylene as raw materials, for example.

Similarly, while a variety of such oxidative processes are known (some being described in references mentioned earlier in this application) and while various methods have been developed for more efficiently separating out the byproduct acetic acid formed in such processes, the present invention is not limited to a particular oxidative process for making acrylic acid or methacrylic acid or to a particular approach to separating out the byproduct acetic acid but can be expected to be of benefit in improving the overall value to the user of any given oxidative process and any particular approach to separating out the byproduct acetic acid that results from that given oxidative process.

This having been said, of course, the present invention can generally be expected to provide the greatest benefit in the context of those processes that have been developed with the particular objective in mind of efficiently separating out the byproduct acetic acid. A number of references may be considered in this regard, including, for example but without limitation, US 2013/0118892 to Meier et al., U.S. Pat. No. 8,273,313 to Galloway, U.S. Pat. No. 7,622,607 to Fauconet et al. and U.S. Pat. No. 6,084,127 to Sakamoto et al.

The conversion of acetic acid to isobutene is illustrated by the following, non-limiting examples:

Example 1

Commercial zirconium hydroxide was dried at 120 degrees Celsius for more than 5 hours. A calculated amount of $Zn(NO_3)_2$ (from Sigma-Aldrich, more than 99.8 percent purity) was dissolved in water, forming a clear solution. The dried zirconium hydroxide (which was also from Sigma-Aldrich, more than 99.8 percent purity) was then mixed with the solution by incipient wetness, in order to form wet powders impregnated with Zn. The wetted powder was then dried at 80 degrees Celsius for 4 hours, followed by calcination at 550 degrees Celsius for 3 hours, to obtain a $Zn_1Zr_8O_z$ catalyst.

An acetic acid to isobutene process was conducted with the catalyst thus prepared in a fixed-bed stainless steel reactor having an inside diameter of 5 millimeters. 100 mg of the catalyst was packed between quartz wool beds. A thermocouple was placed in the middle of the catalyst bed to monitor the reaction temperature. Before beginning the reaction, the catalyst bed was pretreated by flowing 50 ml/minute of nitrogen at 450 degrees Celsius through the catalyst over a half hour. A 25 weight percent solution of acetic acid in water was then introduced into an evaporator at 180 degrees Celsius by means of a syringe pump, and the vaporized steam/acetic acid was carried into the reactor by a flowing nitrogen carrier gas at an acetic acid concentration in the gas phase of 1.36 weight percent and a WHSV of 0.1 grams of acetic acid per gram of catalyst per hour. Meanwhile, the product line was heated to in excess of 150 degrees Celsius before a cold trap, to avoid condensing the liquid products in the product line. A reaction temperature of 415 degrees Celsius was employed.

A Shimadzu 2400 gas chromatograph equipped with an auto sampling valve, HP-Plot Q column (30 m, 0.53 mm, 40 μm) and flame ionization detector was connected to the line between the reactor outlet and cold trap to collect and analyze the products in the effluent gas. After the cold trap, an online micro-GC (MicroGC 3000A equipped with molecular sieves 5A, plot U columns and thermal conductivity detectors) was used to analyze the product gases specifically, using nitrogen as a reference gas.

A consistent product of about 5 percent by weight of methane, about 10 percent by weight of acetone, about 33 percent by weight of carbon dioxide and more than about 50 percent by weight of the desired isobutene product was obtained. No ethylene or propylene was produced. The catalyst showed very high stability over the full duration of the run, with no signs of observable deactivation after more than 1400 minutes of time-on-stream operation.

Examples 2 through 10

For these additional examples of converting acetic acid to isobutene, additional $Zn_xZr_yO_z$ mixed oxide catalysts were prepared both by the incipient wetness method (IW in Table 1 below) but also by the prior art hard template method (HT) described in the Sun et al. journal article (2011), and these were evaluated and the products analyzed using the same apparatus and method described above but under different sets of reaction conditions (as summarized in Table 1 below).

TABLE 1

Further Acetic acid to Isobutene Examples

| Ex # | Catalyst | Zn/Zr ratio | Reaction temp. (° C.) | WHSV ($g_{acetic}/g_{catal}/hr$) | Steam to carbon ratio | $C_{G\text{-}acetic\ acid}$ (wt %) | Acetone selectivity (mol %) | Isobutene selectivity (mol %) |
|---|---|---|---|---|---|---|---|---|
| 2 | HT | 1/15 | 450 | 0.25 | 5 | 1.3 | 30.5 | 41.7 |
| 3 | HT | 1/15 | 450 | 1.14 | 5 | 1.5 | 61.1 | 18.4 |
| 4 | IW | 1/8 | 415 | 0.1 | 5 | 1.4 | 9.8 | 52.5 |
| 5 | IW | 1/10 | 415 | 0.95 | 5 | 22.3 | 50.8 | 20.1 |
| 6 | IW | 1/10 | 450 | 0.16 | 2.5 | 18.8 | 0.7 | 50.6 |
| 7 | IW | 1/10 | 450 | 0.65 | 2.5 | 18.8 | 8.3 | 46.9 |
| 8 | IW | 1/10 | 415 | 0.16 | 2.5 | 18.8 | 5.7 | 57.2 |
| 9 | IW | 1/10 | 415 | 0.33 | 2.5 | 18.8 | 16.4 | 45.3 |
| 10 | IW | 1/10 | 415 | 0.65 | 2.5 | 18.8 | 30.5 | 35.0 |

The invention claimed is:

1. In an oxidative process for producing a crude acrylic acid from a feedstock to be oxidized and wherein acetic acid is produced as a byproduct, the improvement comprising converting at least a portion of the acetic acid to isobutene in the presence of a catalyst, wherein the catalyst is a $Zn_xZr_yO_z$ mixed oxide catalyst.

2. An improved process according to either of claim 1, further comprising converting at least some isobutene to methacrylic acid.

3. An improved process according to either of claim 1, further comprising converting at least some isobutene to isoprene.

4. An improved process according to either of claim 1, further comprising converting at least some isobutene to one or both of methyl tertiary butyl ether and ethyl tertiary butyl ether.

5. An improved process according to either of claim 1, further comprising converting at least some isobutene to isooctane.

6. An improved process according to either of claim 1, further comprising converting at least some isobutene to one or both of butylated hydroxytoluene and butylated hydroxyanisole.

7. An improved process according to claim 1, wherein the mixed oxide catalyst contains less than 0.14 percent by weight of sulfur.

* * * * *